(12) United States Patent
Thornton

(10) Patent No.: US 6,374,824 B1
(45) Date of Patent: *Apr. 23, 2002

(54) DEVICE FOR IMPROVING BREATHING

(76) Inventor: W. Keith Thornton, 5524 Edlen, Dallas,Dallas County, TX (US) 75220

( * ) Notice: Subject to any disclaimer, the term of this patent is extended or adjusted under 35 U.S.C. 154(b) by 0 days.

This patent is subject to a terminal disclaimer.

(21) Appl. No.: 09/290,512

(22) Filed: Apr. 12, 1999

Related U.S. Application Data

(63) Continuation of application No. 08/878,998, filed on Jun. 19, 1997, now Pat. No. 5,983,892, which is a continuation of application No. 08/582,526, filed on Jan. 3, 1996, now abandoned, which is a continuation-in-part of application No. 08/253,949, filed on Jun. 3, 1994, now Pat. No. 5,537,994.

(51) Int. Cl.[7] ............................................... A62B 18/08
(52) U.S. Cl. .......................... 128/201.26; 128/201.18; 128/206.29; 128/204.18; 128/848
(58) Field of Search ..................... 128/201.26, 201.18, 128/206.29, 207.11, 206.21, 848, 859, 860, 204.18

(56) References Cited

U.S. PATENT DOCUMENTS

| 690,663 A | 1/1902 | Pratt |
|---|---|---|
| 746,869 A | 12/1903 | Moulton |
| 774,446 A | 11/1904 | Moulton |
| 885,196 A | 4/1908 | Steil |

(List continued on next page.)

FOREIGN PATENT DOCUMENTS

| AU | B-78762/94 | 9/1994 | ......... A61F/005/56 |
|---|---|---|---|
| AU | B-27647/95 | 2/1995 | ......... A62B/018/08 |
| DE | 156627 | 12/1904 | |
| DE | 2320501 | 11/1974 | ............. A61F/5/56 |
| DE | 3707952 A1 | 12/1987 | .......... A61M/16/06 |
| DE | 29506512 | 6/1995 | |
| DE | 19524534 C1 | 5/1996 | .......... A61M/16/04 |
| EP | 0312368 | 4/1989 | ............. A61F/5/56 |
| EP | 0359135 | 3/1990 | ........... A63B/71/10 |
| GB | 1569129 | 6/1980 | ............. A61F/5/56 |
| WO | WO 98/20924 | 5/1998 | .......... A61M/15/08 |

OTHER PUBLICATIONS

English translation of German Patent Specification No. 295 06 512.5 (Erkodent Erich Kopp GmbH), Apr. 11, 1995.
Mayo Clinic Health Letter, vol. 13, No. 7, "Snoring.", Jul. 1995.
Photocopies of 2–piece dental device manufactured by Currie–Gibson Dental Laboratory, Inc. prior to Apr. 13, 1993.

(List continued on next page.)

*Primary Examiner*—John G. Weiss
*Assistant Examiner*—V. Srivastava
(74) *Attorney, Agent, or Firm*—Baker Botts L.L.P.

(57) ABSTRACT

A device for improving the breathing of a user includes an upper arch (12) adapted to receive at least some of the user's upper teeth, a lower arch (14) adapted to receive at least some of the user's lower teeth, a connector (16) adjustably coupling the lower arch (14) to the upper arch (12), a support surface (54) positioned forwardly, relative to the lower arch (14), and a tensile member (48). The tensile member (48) has first and second ends, in which the first end of the tensile member (48) adjustably couples to the connector (16), and the second end of the tensile member (48) couples to the lower arch (14). The tensile member (48) contacts the support surface (54) along a contact region of the tensile member (48) located between the first and second ends of the tensile member (48). The connector (16) is operable to adjustably position the lower arch (14) forwardly, relative to the upper arch (12), by exerting a tensile force upon the lower arch (14). The connector (16) is also operable to allow lateral motion of the lower arch (14) relative to the upper arch (12) and to adjustably position the lower arch (14) vertically relative to the upper arch (12).

18 Claims, 6 Drawing Sheets

U.S. PATENT DOCUMENTS

| | | | |
|---|---|---|---|
| 1,076,534 A | 10/1913 | Wallen | |
| 1,146,264 A | 7/1915 | Kelly | |
| 1,483,694 A | 2/1924 | Stukey | |
| 1,649,664 A | 11/1927 | Carter | |
| 1,674,336 A | 6/1928 | King | |
| 2,171,695 A | 9/1939 | Harper | 32/19 |
| 2,178,128 A | 10/1939 | Waite | 128/136 |
| 2,424,533 A | 7/1947 | Faires | 128/136 |
| 2,521,039 A | 9/1950 | Carpenter | 128/136 |
| 2,531,222 A | 11/1950 | Kesling | 32/14 |
| 2,574,623 A | 11/1951 | Clyde | 128/136 |
| 2,590,118 A | 3/1952 | Oddo, Jr. | 128/136 |
| 2,627,268 A | 2/1953 | Leppich | 128/136 |
| 2,833,278 A | 5/1958 | Ross | 128/136 |
| 2,867,212 A | 1/1959 | Nunn, Jr. | 128/136 |
| 2,882,893 A | 4/1959 | Godfroy | 128/136 |
| 3,037,501 A | 6/1962 | Miller | 128/141 |
| 3,107,668 A | 10/1963 | Thompson | 128/136 |
| 3,124,129 A | 3/1964 | Grossberg | 128/136 |
| 3,132,647 A | 5/1964 | Corniello | 128/136 |
| 3,219,033 A | 11/1965 | Wallshein | 128/136 |
| 3,277,892 A | 10/1966 | Tepper | 128/172.1 |
| 3,312,216 A | 4/1967 | Wallshein | 128/136 |
| 3,321,832 A | 5/1967 | Weisberg | 32/32 |
| 3,434,470 A | 3/1969 | Strickland | 128/136 |
| 3,457,916 A | 7/1969 | Wolicki | 128/136 |
| 3,513,838 A | 5/1970 | Foderick et al. | 128/136 |
| 3,522,805 A | 8/1970 | Wallshein | 128/136 |
| 3,658,058 A | 4/1972 | Neidhart et al. | 128/147 |
| 3,864,832 A | 2/1975 | Carlson | 128/136 |
| 3,871,370 A | 3/1975 | McDonald | 128/136 |
| 3,884,226 A | 5/1975 | Tepper | 128/136 |
| 4,016,650 A | 4/1977 | Leusner et al. | 32/17 |
| 4,026,024 A | 5/1977 | Tradowsky | 32/19 |
| 4,114,614 A | 9/1978 | Kesling | 128/136 |
| 4,169,473 A | 10/1979 | Samelson | 128/136 |
| 4,182,312 A | 1/1980 | Mushabac | 433/68 |
| 4,227,877 A | 10/1980 | Tureaud et al. | 433/37 |
| 4,233,972 A | 11/1980 | Hauff et al. | 128/205 |
| 4,289,127 A | 9/1981 | Nelson | 128/207.14 |
| 4,304,227 A | 12/1981 | Samelson | 128/136 |
| 4,345,592 A | 8/1982 | Giorgini et al. | 128/204 |
| 4,345,593 A | 8/1982 | Sullivan | 128/204 |
| 4,376,628 A | 3/1983 | Aardse | 433/80 |
| 4,382,783 A | 5/1983 | Rosenberg | 433/19 |
| 4,392,490 A | 7/1983 | Mattingly et al. | 128/202 |
| 4,433,956 A | 2/1984 | Witzig | 433/7 |
| 4,439,147 A | 3/1984 | Magill et al. | 433/3 |
| 4,439,149 A | 3/1984 | Devincenzo | 433/6 |
| 4,470,413 A | 9/1984 | Warncke | 128/201.18 |
| 4,495,945 A | 1/1985 | Liegner | 128/200.26 |
| 4,505,672 A | 3/1985 | Kurz | 433/6 |
| 4,553,549 A | 11/1985 | Pope et al. | 128/421 |
| 4,568,280 A | 2/1986 | Ahlin | 433/6 |
| 4,569,342 A | 2/1986 | von Nostitz | 128/136 |
| 4,593,686 A | 6/1986 | Lloyd et al. | 128/136 |
| 4,602,905 A | 7/1986 | O'Keefe, III | 433/41 |
| 4,639,220 A | 1/1987 | Nara et al. | 433/69 |
| 4,655,213 A | 4/1987 | Rapoport et al. | 128/205.25 |
| 4,669,459 A | 6/1987 | Spiewak et al. | 128/136 |
| 4,676,240 A | 6/1987 | Gardy | 128/207.14 |
| 4,706,683 A | 11/1987 | Chilton et al. | 128/654 |
| 4,715,368 A | 12/1987 | George | 128/136 |
| 4,773,853 A | 9/1988 | Kussick | 433/6 |
| 4,799,500 A | 1/1989 | Newbury | 128/859 |
| 4,858,606 A | 8/1989 | Hamlin | 128/204 |
| 4,862,903 A | 9/1989 | Campbell | 128/861 |
| 4,870,962 A | 10/1989 | Sitnik | 128/205 |
| 4,886,056 A | 12/1989 | Simpson | 128/201 |
| 4,901,737 A * | 2/1990 | Toone | 128/848 |
| 4,906,234 A | 3/1990 | Voychehovski | 604/79 |
| 4,919,128 A | 4/1990 | Kopala et al. | 128/207.18 |
| 4,932,867 A | 6/1990 | Ueno | 433/69 |
| 4,955,393 A | 9/1990 | Adell | 128/859 |
| RE33,442 E | 11/1990 | George | 128/860 |
| 5,003,994 A | 4/1991 | Cook | 128/848 |
| 5,018,533 A | 5/1991 | Hawkins | 128/848 |
| 5,028,232 A | 7/1991 | Snow | 433/24 |
| 5,042,478 A | 8/1991 | Kopala et al. | 128/207.18 |
| 5,042,506 A | 8/1991 | Liberati | 128/848 |
| 5,046,512 A | 9/1991 | Murchie | 128/848 |
| 5,052,409 A | 10/1991 | Tepper | 128/859 |
| 5,056,534 A | 10/1991 | Wright | 128/848 |
| 5,065,756 A | 11/1991 | Rapoport | 128/204 |
| 5,078,600 A | 1/1992 | Austin | 433/73 |
| 5,092,346 A | 3/1992 | Hays et al. | 128/848 |
| 5,103,838 A | 4/1992 | Yousif | 128/859 |
| 5,117,816 A | 6/1992 | Shapiro et al. | 128/200.24 |
| RE35,339 E | 10/1992 | Rapoport | 128/204 |
| 5,154,184 A | 10/1992 | Alvarez | 128/848 |
| 5,154,609 A | 10/1992 | George | 433/68 |
| 5,183,057 A | 2/1993 | Syrop et al. | 128/845 |
| 5,188,529 A | 2/1993 | Lüth | 433/68 |
| 5,193,532 A | 3/1993 | Moa et al. | 128/204 |
| 5,243,971 A | 9/1993 | Sullivan et al. | 128/205 |
| 5,245,995 A | 9/1993 | Sullivan et al. | 128/204 |
| 5,267,862 A | 12/1993 | Parker | 433/215 |
| 5,277,202 A | 1/1994 | Hays | 128/848 |
| 5,284,161 A | 2/1994 | Karell | 128/848 |
| 5,313,960 A | 5/1994 | Tomasi | 128/848 |
| 5,316,020 A | 5/1994 | Truffer | 128/848 |
| 5,365,945 A | 11/1994 | Halstrom | 128/848 |
| 5,373,859 A | 12/1994 | Forney | 128/846 |
| 5,409,017 A | 4/1995 | Lowe | 128/848 |
| 5,456,264 A | 10/1995 | Series et al. | 128/725 |
| 5,458,137 A | 10/1995 | Axe et al. | 128/204 |
| 5,477,850 A | 12/1995 | Zegler et al. | 128/202 |
| 5,503,146 A | 4/1996 | Froehlich et al. | 128/204 |
| 5,537,994 A * | 7/1996 | Thornton | 128/204.18 |
| 5,537,999 A | 7/1996 | Dearman et al. | 128/205 |
| 5,538,000 A | 7/1996 | Rudolph | 128/205 |
| 5,551,419 A | 9/1996 | Froehlich et al. | 128/204 |
| 5,558,090 A | 9/1996 | James | 128/207.18 |
| 5,560,354 A | 10/1996 | Berthon-Jones et al. | 128/205 |
| 5,592,935 A | 1/1997 | Elstran et al. | 128/205 |
| 5,611,485 A | 3/1997 | Davis | 239/8 |
| 5,657,751 A | 8/1997 | Karr, Jr. | 128/205 |
| 5,657,752 A | 8/1997 | Landis et al. | 128/207 |
| 5,676,133 A | 10/1997 | Hickle et al. | 128/205 |
| 5,678,567 A | 10/1997 | Thornton et al. | 128/848 |
| 5,687,715 A | 11/1997 | Landis et al. | 128/207.18 |
| 5,713,349 A | 2/1998 | Keaney | 128/204 |
| 5,718,244 A | 2/1998 | Thronton | 128/864 |
| 5,718,500 A | 2/1998 | Vinci guerra et al. | 2/431 |
| 5,720,280 A | 2/1998 | Elstran et al. | 128/205 |
| 5,720,302 A * | 2/1998 | Belfer | 128/848 |
| 5,746,201 A | 5/1998 | Kidd | 128/206 |
| 5,752,510 A | 5/1998 | Goldstein | 128/207 |
| 5,755,219 A * | 5/1998 | Thornton | 128/201.18 |
| 5,807,100 A | 9/1998 | Thornton | 433/48 |
| 5,829,441 A | 11/1998 | Kidd et al. | 128/848 |
| 5,846,082 A | 12/1998 | Thornton | 433/215 |
| 5,887,587 A | 3/1999 | Groenke | 128/207 |
| 5,919,042 A * | 7/1999 | Williams | 433/19 |
| 5,947,724 A * | 9/1999 | Frantz et al. | 433/19 |
| 5,954,048 A * | 9/1999 | Thornton | 128/201.18 |
| 5,980,247 A * | 11/1999 | Cleary | 433/19 |
| 5,983,892 A * | 11/1999 | Thornton | 128/201.26 |
| 5,988,166 A | 11/1999 | Hayek | 128/205 |
| 6,012,455 A * | 1/2000 | Goldstein | 128/207.18 |
| 6,027,340 A * | 2/2000 | Chun | 433/19 |

6,109,265 A * 8/2000 Frantz et al. ............... 128/848

OTHER PUBLICATIONS

Farrar & McCarty, "A Clinical Outline of Temporomandibular Joint Diagnosis and Treatment," Normandie Study Group for TMJ Dysfunction, 3 pages, 1983.

Professional Positioners brochure, "Dedicated to Excellence," 4 pages.

Great Lakes Orthodontics, Ltd., "Nocturnal Airway Patency Appliance™ (NAPA),".

Schmidt–Nowara, et al., "Oral Appliances for the Treatment of Snoring and Obstructive Sleep Apnea: A Review," Sleep, 18(6):501–510., 1995.

George, "Treatment of Snoring and Obstructive Sleep Apnea with a Dental Device," General Dentistry, 5 pages, Jul.–Aug. 1993.

Database WOI, Section PQ, Week 9039, Derwent Publication, Ltd., London, GB XP–002116355 –Abstract "Surgical Mouth Air Duct.", Dec. 15 1989.

CPAP/PRO®... Introducing a New Comfort Level for CPAP Users!!brochure(2 pages).

W. Keith Thornton, "Combination Face Mask and Dental Device for Improved Breathing During Sleep," USSN 08/594,904 filed Jan. 31 1996 (019651.0129).

W. Keith Thornton, "Method and Apparatus for Adjusting a Dental Device," U.S. Appln. Serial No. 08/787,529, pending(019651.0152)., Jun. 15 1999.

W. Keith Thornton, "Apparatus for Prevention of Snoring and Improved Breathing During Sleep," U.S. Appln. Serial No. 08/828,523, pending(019651.0154)., Mar. 31 1997.

W. Keith Thornton, "Method and Apparatus for Adjusting a Dental Device, " U.S. Appln. Serial No. 08/787,529, pending(019651.0166)., Jan. 21 1997.

W. Keith Thornton, "Device for Improving Breathing and Method for Fitting Same," U.S. Appln. Serial No. 09/396,986, pending(019651.0175)., Sep. 15 1999.

W. Keith Thornton, "Oral Appliance Having a Bonding Layer and Method for Fitting and Relining Same," USSN 09/483,741(019651.0175), Jul. 17 2000.

* cited by examiner

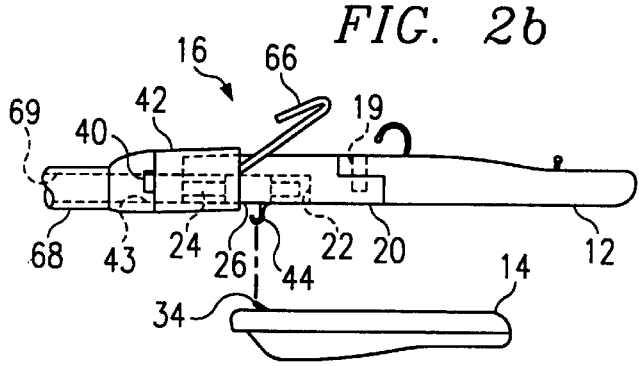
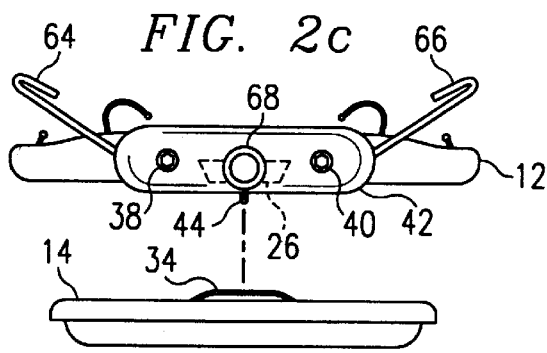
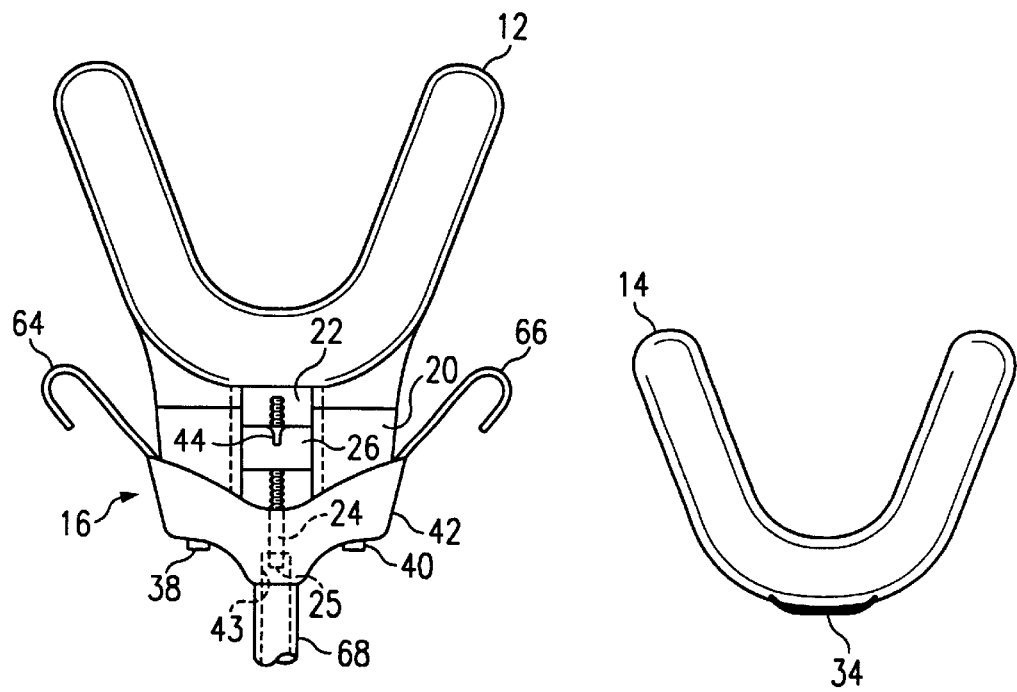

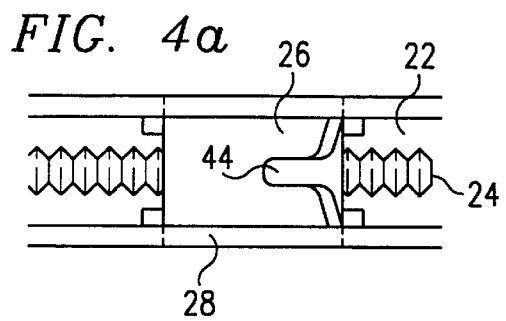
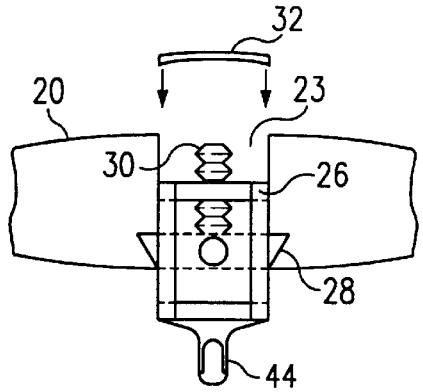
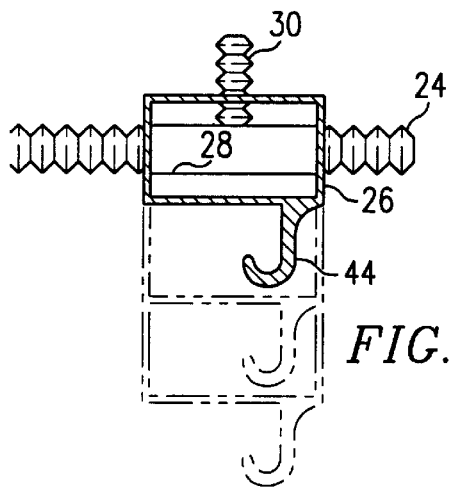
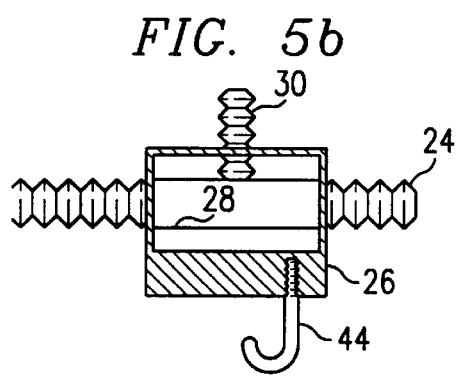
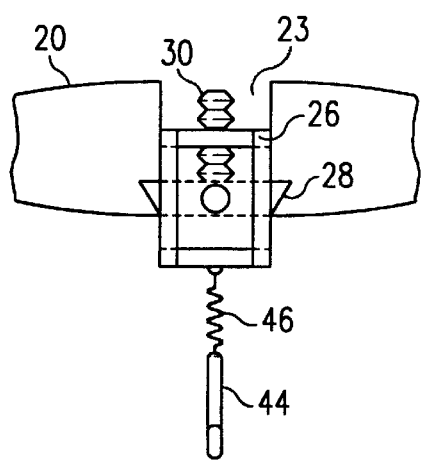
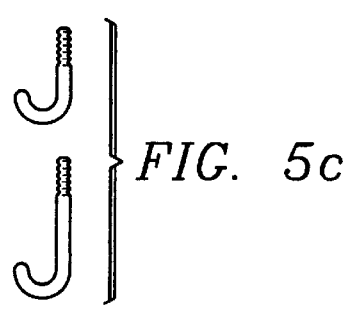

DEVICE FOR IMPROVING BREATHING

CROSS-REFERENCE TO RELATED APPLICATIONS

This application is a continuation of U.S. application Ser. No. 08/878,998 filed Jun. 19, 1997 by W. Keith Thornton and entitled "Device for Improving Breathing", now U.S. Pat. No. 5,983,892 which is a continuation of U.S. application Ser. No. 08/582,526, filed Jan. 3, 1996 by W. Keith Thornton and entitled "Device for Improving Breathing", abandoned; which is a continuation-in-part of U.S. application Ser. No. 08/253,949 filed Jun. 3, 1994 and entitled "Combination Face Mask and Dental Device for Improved Breathing During Sleep", now U.S. Pat. No. 5,537,994 issued Jul. 23, 1996.

This application is also related to U.S. application Ser. No. 08/501,437 filed Jul. 12, 1995 by W. Keith Thornton and Andrew O. Jamieson and entitled "Apparatus for Adjusting a Dental Device," now U.S. Pat. No. 5,678,567 issued Oct. 21, 1997; which is a continuation of U.S. application Ser. No. 08/435,277 filed May 5, 1995 by W. Keith Thornton and Andrew O. Jamieson and entitled "Method and Apparatus for Adjusting a Dental Device", abandoned; which is a continuation of U.S. application Ser. No. 08/218,719 filed Mar. 25, 1994 by W. Keith Thornton and Andrew O. Jamieson and entitled "Method and Apparatus for Adjusting a Dental Device.," abandoned.

TECHNICAL FIELD OF THE INVENTION

This invention relates generally to medical devices, and more particularly to a device for improving breathing.

BACKGROUND OF THE INVENTION

Many people experience breathing problems. These problems may result in difficulty sleeping, in snoring, or in more serious conditions such as sleep apnea.

One treatment for breathing disorders involves the use of devices inserted into the mouth for extending forward the lower jaw of the patient. These devices open the breathing passageway more fully and allow easier breathing through the nose and mouth. These devices may treat some breathing problems, but may not sufficiently treat more serious conditions such as sleep apnea.

Another treatment for breathing disorders involves application of continuous positive air pressure ("CPAP") to the patient. The CPAP is delivered through a face mask, nose mask, or nasal inserts, and results in a fuller opening of the patient's breathing passageway. The CPAP may be increased for more serious conditions. Face masks for delivering CPAP are commonly secured to the patient's head with an adjustable or elastic strap. As the patient moves, the face mask often shifts and unseats from the patient's face, which may reduce the CPAP or awaken a sleeping patient.

SUMMARY OF THE INVENTION

In accordance with the teachings of the present invention, a device is provided which substantially reduces or eliminates the disadvantages and problems associated with prior art devices for improving breathing.

In particular, a device for improving breathing is provided which includes an upper arch adapted to receive at least some of a user's upper teeth, a lower arch adapted to receive at least some of a user's lower teeth, and a connector adjustably coupling the lower arch to the upper arch. The connector is operable to allow lateral motion of the lower arch relative to the upper arch, and to adjustably position the lower arch forwardly, relative to the upper arch. In another embodiment, the connector is operable to adjustably position the lower arch vertically, relative to the upper arch, and includes a hooking element operable to removably engage the lower arch.

In a further embodiment, the connector is removably coupled to the upper arch. In another embodiment, the connector includes a lip bumper. In yet another embodiment, the upper and lower arches are adapted to receive a deformable material in which molds of at least some of a user's upper and lower teeth, respectively, may be formed.

In another embodiment, the connector is operable to allow lateral motion of the lower arch relative to the upper arch, and to adjustably position the lower arch forwardly, relative to the upper arch, by exerting a tensile force upon the lower arch.

In a further embodiment, a device for improving breathing is provided which includes an upper arch adapted to receive at least some of a user's upper teeth, a lower arch adapted to receive at least some of a user's lower teeth, and a connector adjustably coupling the lower arch to the upper arch. The connector is operable to adjustably position the lower arch forwardly, relative to the upper arch, by exerting a tensile force upon the lower arch. The device also includes a support surface positioned forwardly, relative to the lower arch, and a tensile member having first and second ends. The first end of the tensile member is adjustably coupled to the connector, the second end of the tensile member is coupled to the lower arch, and the tensile member contacts the support surface along a contact region of the tensile member that is located between its first and second ends.

Another embodiment provides a device for improving breathing which includes an upper arch adapted to receive at least some of a user's upper teeth, and a tongue engager adjustably coupled to the upper arch. The tongue engager is operable to engage the user's tongue and to adjustably position the tongue thereby.

Yet another embodiment of the present invention provides a device for improving breathing which includes an upper arch adapted to receive at least some of a user's upper teeth, a connector operable to allow lateral motion of a user's lower jaw relative to the upper arch and to adjustably position the lower jaw forwardly relative to the upper arch, a face mask, a system for supplying gas to the face mask, and a connecting apparatus operable to adjustably couple the face mask to the upper arch. In a further embodiment, the connecting apparatus is operable to allow universal movement between the upper arch and the face mask.

An important technical advantage of the present invention is that a face mask is anchored by customizable arches, thereby providing a more secure fit for the face mask on the user's face. Because the embodiments may include removable arches that are customizable by the user as well as by a clinical professional, the present invention may be less expensive than would otherwise be possible. A lip bumper may also be provided which allows the user's lips to form a seal around a portion of the device that includes the upper arch, thereby allowing the CPAP system to work more effectively. The lip bumper also provides additional comfort by reducing fatigue that may result from a user's tendency to form his or her lips more tightly around an object whose cross-section is smaller than the opening formed by the user's lips when they are in a relaxed state.

Another important technical advantage of the present invention is the fact that it allows a user's lower jaw to be adjustably positioned forwardly relative to the user, while permitting the jaw to move laterally. In particular embodiments, forward adjustment is done from a point forward relative to the jaw, thereby reducing the upward vertical load experienced by the lower arch and the likelihood that the lower arch will be pulled off of the lower teeth when the user's lower jaw is moved. Still other embodiments eliminate this contingency entirely by engaging the tongue directly in order to position the tongue forwardly relative to the upper arch. The present invention increases the opening of the user's breathing passageway, and consequently increases the effectiveness of the treatment for breathing disorders such as sleep apnea, while remaining more comfortable for the user.

BRIEF DESCRIPTION OF THE DRAWINGS

For a more complete understanding of the present invention and its advantages, reference is now made to the following descriptions taken in conjunction with the accompanying drawings, in which like reference numbers indicate like features and wherein:

FIGS. 2a–2d illustrate bottom isometric, side, front, and bottom views of the device illustrated in FIG. 1;

FIGS. 4a–4c illustrate exploded bottom, front, and side views of a hooking element constructed according to the teachings of the present invention;

FIGS. 5a–5d illustrate exploded side views of alternative embodiments of the present invention adapted for use in connection with alternative hooking elements and a flexible member;

DETAILED DESCRIPTION OF THE INVENTION

Figure 1A:
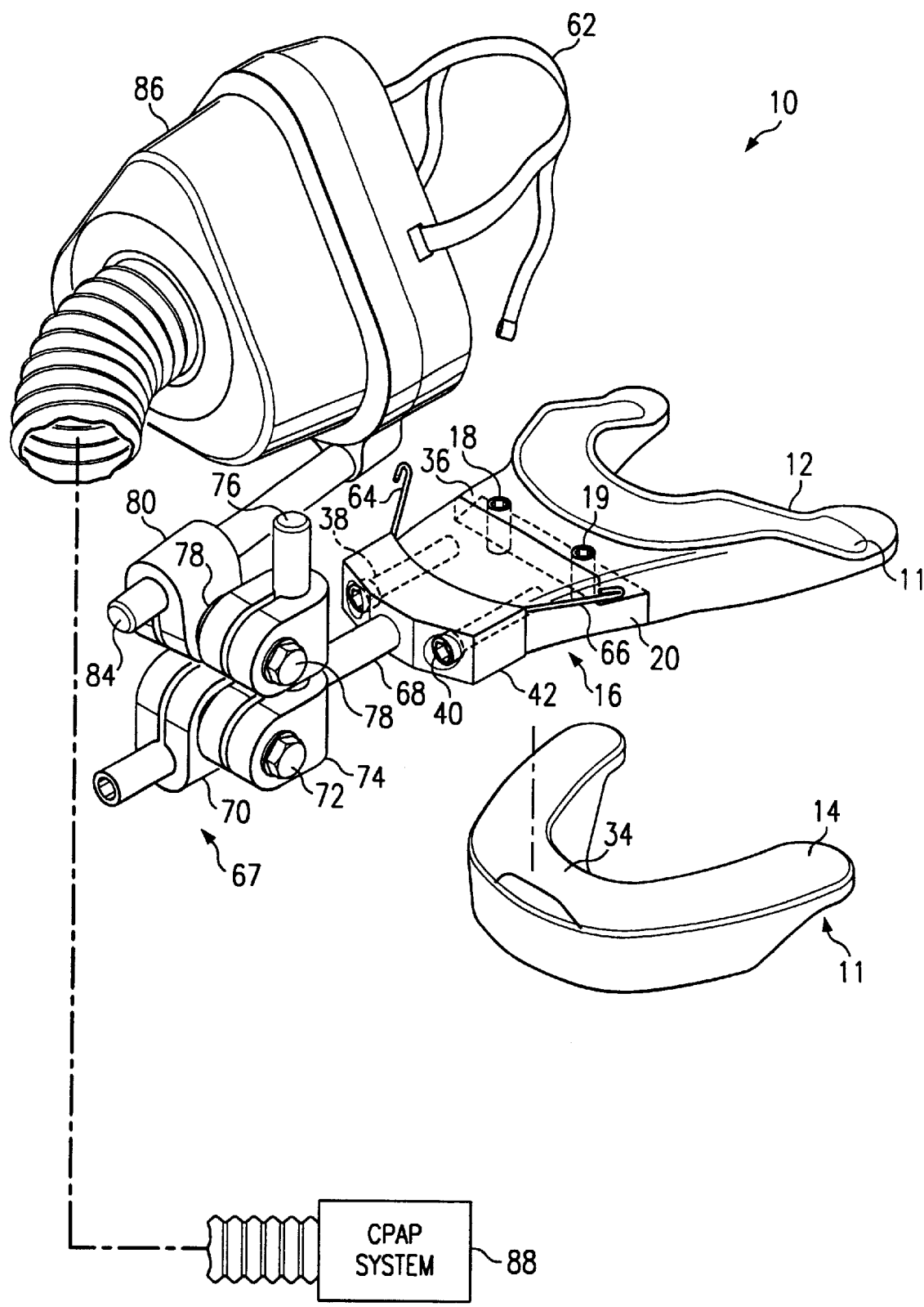
FIG. 1a illustrates an isometric view of a device for improving breathing constructed according to the teachings of the present invention.

FIG. 1a illustrates a device for improving breathing constructed according to the teachings of the present invention. Device 10 is provided with an upper arch 12 and a lower arch 14. Upper arch 12 is adapted to receive at least some of a user's upper teeth, and lower arch 14 is adapted to receive at least some of the user's lower teeth. When device 10 is in use, upper arch 12 and lower arch 14 are inserted into the user's mouth.

Upper arch 12 and lower arch 14 are adapted to receive a deformable material 11 in which molds of at least some of the user's upper and lower teeth, respectively, may be formed. Deformable material 11 may be the ethylene-vinyl acetate copolymer resin sold under the name ELVAX®, or another suitable deformable material that can be used to form molds of a user's teeth. In one embodiment, deformable material 11 is heated to a temperature of about one hundred and fifty degrees Fahrenheit, using a microwave oven or hot water, for example, so as to place deformable material 11 in its deformable state. Upper arch 12 and lower arch 14 are then inserted into the user's mouth, either separately or together, and the user bites down to deform deformable material 11 into the shape of the user's teeth. Upper arch 12 and lower arch 14 are then removed and allowed to cool and harden. The present invention is therefore readily customizable by the user.

Figure 1B:
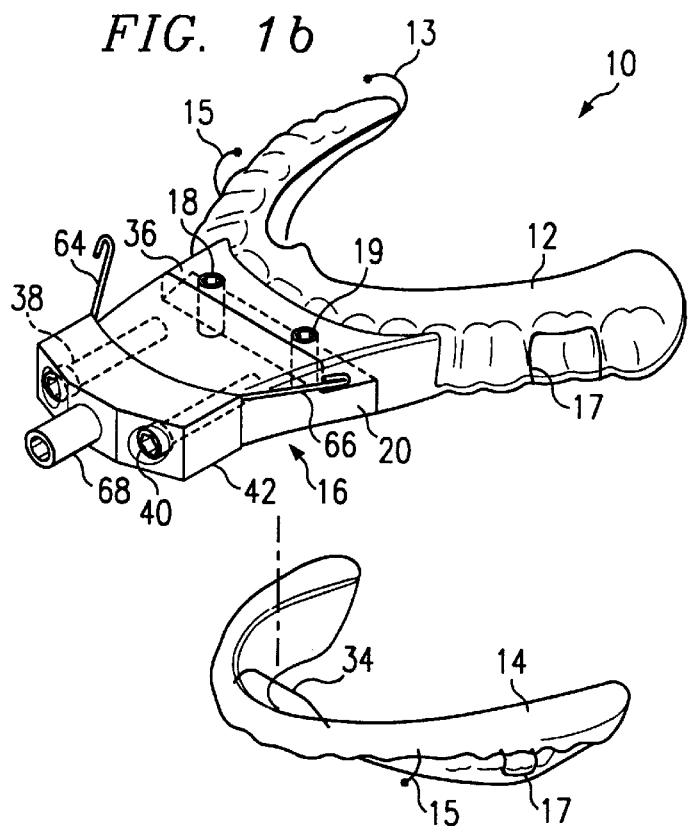
FIG. 1b illustrates an alternative embodiment of the present invention adapted for use in connection with alternative upper and lower arches.
Figure 2A:
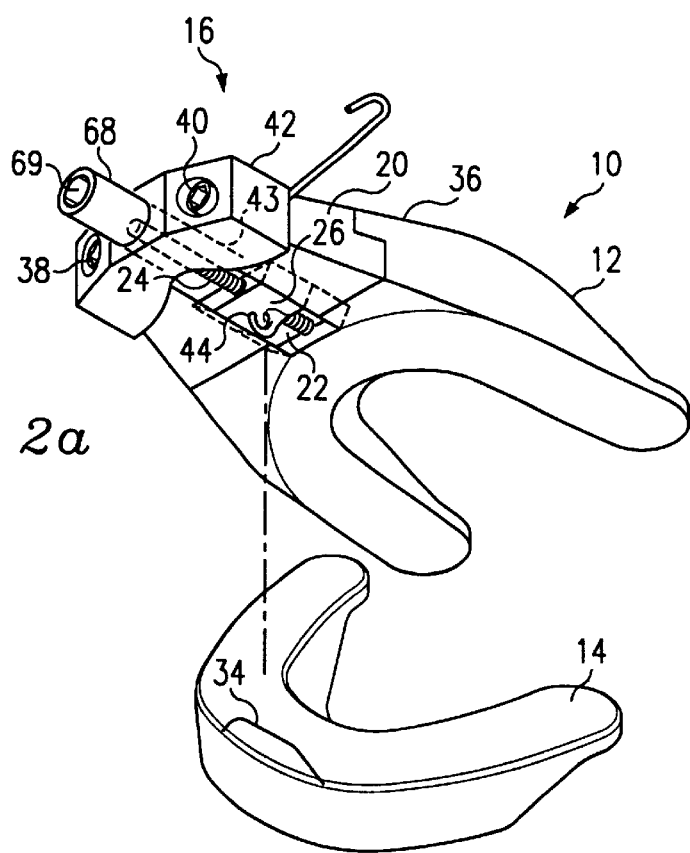

Alternatively, as shown in FIG. 1b, upper arch 12 and lower arch 14 may themselves be formed from a deformable material suitable for dental uses, such as methyl methacrylate or a polycarbonate resin thermoplastic such as that sold under the name LEXAN®. Such materials are known to those familiar with dental mouthpieces, and other materials may be used without departing from the intended scope of the present invention. Thus, the present invention is also readily customizable by a clinical professional.

Various securing clasps can be used to more fully secure upper arch 12 and lower arch 14 to the user's teeth. Illustrative embodiments include C-clasps 13, ball clasps 15, and U-clasps 17. One or more of securing clasps 13, 15, and 17 may be included on upper arch 12 and lower arch 14.

Upper arch 12 is coupled to the remainder of device 10 using connector 16. The body 20 of connector 16 is removably coupled to upper arch 12 using screws 18 and 19. Other fastening agents may be employed without departing from the intended scope of the present invention. Although upper arch 12 is removably coupled to body 20 of connector 16, the present invention also contemplates an integral piece of material that forms both body 20 and upper arch 12 without the need for fastening agents.

An important advantage of the present invention is that body 20 of connector 16 is removable from upper arch 12. This allows a mold of the user's upper teeth to be formed before device 10 is assembled and secured to the user. Similarly, as discussed more fully below, lower arch 14 is removably coupled to connector 16. Lower arch 14 may therefore include a mold of the user's lower teeth that is formed before device 10 is assembled and secured to the user. Because upper arch 12 and lower arch 14 are removably coupled to connector 16, and are therefore removably coupled to the remainder of device 10, the present invention may be customized by either the user or by a clinical professional without involving the remainder of device 10.

Connector 16 may provide a lip bumper 36 that allows the user's lips to form a seal around body 20. Lip bumper 36 reduces fatigue that may result from a user's tendency to form his or her lips tightly around an object whose cross-section is smaller than the opening formed by the user's lips when they are in a relaxed state. Lip bumper 36 also provides a more effective seal between the user's lips and body 20 to increase the effectiveness of the CPAP system discussed more fully below. Lip bumper 36 may be integral to or separate from connector 16. Alternatively, lip bumper 36 may be provided by upper arch 12 rather than by connector 16 when, for example, necessitated by the location of the coupling between upper arch 12 and connector 16. Lip bumper 36 may be integral to or separate from upper arch 12 in such a case.

Body 20 is coupled to face plate 42 using screws 38 and 40, or other suitable fastening agents. It should be understood that the present invention contemplates, as an alternative embodiment, an integral piece of material that forms both body 20 and face plate 42 without the need for fastening agents.

Device 10 may be adapted for use in connection with a face mask 86 and a continuous positive air pressure ("CPAP") system 88 for supplying a gas to face mask 86. Face mask 86 may be configured so as to allow gas to be supplied by CPAP system 88 at constant positive air pressure, or at a positive air pressure adjusted accordingly for the particular user or breathing disorder being treated. In general, increasing the air pressure delivered by CPAP system 88 increases the opening of the breathing passageway. CPAP system 88 is shown as an example only. Other systems for delivering any breathable gas, such as air, oxygen, or gases used in anaesthesia, at constant or varying pressures may also be used. Face mask 86 should be configured so as to allow the gas exhaled by the patient to be exhausted from face mask 86.

According to one embodiment of the present invention, an adjustable strap 62 may be included with device 10. Adjustable strap 62 is operable to engage strap hooks 64 and 66, which are coupled to face plate 42 of connector 16. Adjustable strap 62 operates to secure device 10 to the user's head, and consequently allows the user's lower jaw to be extended forward with less stress placed on the user's upper jaw and less risk of injury to the user's teeth. Adjustable strap 62 also increases the effectiveness of CPAP system 88 in delivering gas to face mask 86. Adjustable strap 62 need not engage both or either of strap hooks 64 and 66, and may instead attach only to face mask 86. Conversely, adjustable strap 62 may be attached only to a portion of connector 16, such as strap hooks 64 and 66, but not to face mask 86. Other methods of coupling adjustable strap 62 to device 10 may also be used.

In another embodiment of the present invention, face mask 86 is adjustably coupled to connector 16 and therefore to upper arch 12 using connecting apparatus 67. Connecting apparatus 67 includes a hollow post 68 that extends forward from face plate 42. Hollow post 68 meets and engages swivel collar 70, forming an adjustable collar joint through which hollow post 68 may slide and rotate. Fastener 72 couples swivel collars 70 and 74 at a desired angle relative to one another. Connecting post 76 extends at one end through swivel collar 74, forming a second adjustable collar joint through which connecting post 76 may slide and rotate. When fastener 72 is tightened, the two collar joints formed by collars 70 and 74 with hollow post 68 and connecting post 76, respectively, are tightened.

Connecting post 76 extends at the other end through collar 78, forming a third adjustable collar joint through which connecting post 76 may slide and rotate. Fastener 80 couples swivel collars 78 and 82 at a desired angle relative to one another. Post 84 extends at its distal end through swivel collar 82, forming a fourth collar joint through which post 84 may slide and rotate. When fastener 80 is tightened, the collar joints formed by swivel collars 78 and 82 with connecting post 76 and post 84, respectively, are tightened.

Post 84 is secured to face mask 86 at its proximal end, completing the coupling of connector 16 to face mask 86. The present invention thereby provides universal adjustability, allowing the portion of device 10 that is coupled to the user's mouth to be adjustably positioned forward, vertically, laterally, angularly, and rotationally with respect to face mask 86, providing an important technical advantage. It should be understood that other suitable methods of providing universal adjustability exist and may be employed with device 10 without departing from the intended scope of the present invention.

FIGS. 2a–2d illustrate a body 20 of connector 16 having a channel 22. Hooking element 26 is adapted to fit in channel 22 and to slide along the length of channel 22. Horizontal screw 24 extends from the front of body 20 rearward into channel 22 to engage hooking element 26. Screw head 25 of horizontal screw 24 may be accessed using a horizontal hole 43 formed in face plate 42.

A screwdriver or other suitable adjustment device may be inserted into horizontal hole 43 in face plate 42 to engage screw head 25. The hollow portion 69 of hollow post 68, which is coupled to connector 16 through face plate 42, provides access to horizontal hole 43 and to screw head 25. Horizontal screw 24 may extend forward through face plate 42 and into hollow portion 69, may extend only into horizontal hole 43 and not into hollow portion 69, or rest only within body 20 and not extend into horizontal hole 43.

In one embodiment, at least a portion of the side walls of channel 22 are formed diagonally so as to guide the travel of hooking element 26 forward or rearward within channel 22 when horizontal screw 24 is turned, while not allowing hooking element 26 to displace vertically. Hooking element 26 slides forward or rearward within channel 22 in response to horizontal screw 24 being turned in the appropriate direction. The present invention contemplates side walls of channel 22 that are formed in any manner suitable to allow hooking element 26 to travel forward or rearward within channel 22, while not allowing hooking element 26 to displace vertically.

Lower arch 14 includes a hooking clasp 34, which extends laterally across the midline of lower arch 14 and is operable to engage hook 44. While engaged with hook 44, lower arch 14 may move laterally in response to lateral motions of the user's jaw. Hook 44 may be integral to or separate from hooking element 26. Hooking clasp 34 is shown with a substantially circular cross-section that allows coupling between hooking clasp 34 and hook 44, but other cross-sections of hooking clasp 34 and manners of coupling hooking element 26 and hooking clasp 34 may be used without departing from the intended scope of the present invention.

Due to the relative positions of hook 44 and hooking clasp 34, when hook 44 has engaged hooking clasp 34, lower arch 14 and thus the user's lower jaw may be extended forward, relative to upper arch 12. When horizontal screw 24 is turned in the appropriate direction, lower arch 14 and thus the user's lower jaw may be adjusted forward or rearward so as to be extended forward to the extent desired, relative to upper arch 12. The amount of forward extension may be increased or decreased as necessary to properly size device 10 to the user and to effectively treat the breathing disorder involved. In another embodiment, hooking element 26 is allowed to move freely through channel 22 unless a vertical screw or other suitable member is adjusted to contact hooking element 26 within channel 22 and thereby press hooking element 26 against the inner surface of channel 22 with a force sufficient to secure hooking element 26 in the desired position. Hooking element 26 may be further adjusted by reducing or releasing the force pressing hooking element 26 against channel 22, moving hooking element 26 to the desired position, and then reapplying the force to hooking element 26. The present invention contemplates alternate embodiments wherein the lower jaw is adjusted using a motor or hydraulics. Such a motor or hydraulics may be used in connection with horizontal screw 24, but need not be used in connection with horizontal screw 24 to be within the intended scope of the present invention.

Figure 3A:
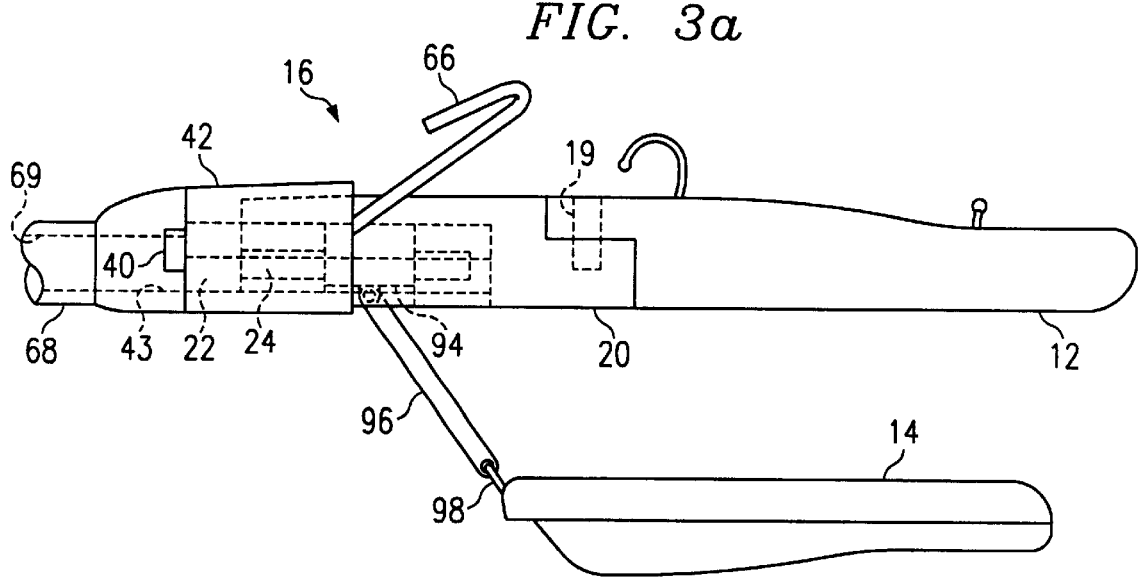
FIGS. 3a and 3b illustrate side and front views of an alternate embodiment of the present invention adapted for use in connection with a slider.
Figure 3B:
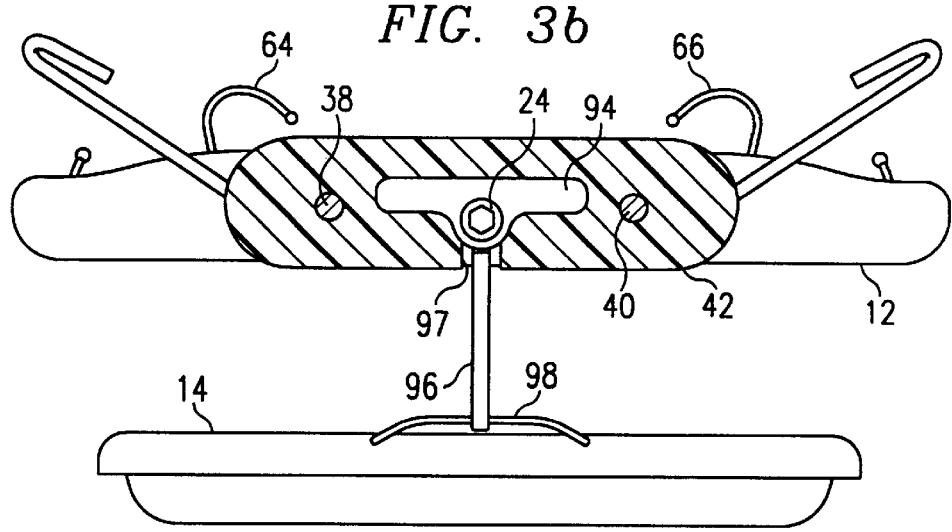

FIGS. 3a and 3b illustrate side and front views of an alternate embodiment of the present invention adapted for use in connection with a slider 94. Slider 94 is adapted to fit in channel 22 and to slide along the length of channel 22. Horizontal screw 24 extends from the front of body 20 rearward into channel 22 to engage slider 94. Screw head 25 of horizontal screw 24 may be accessed and adjusted as described above in connection with FIGS. 2a–2d.

In one embodiment, at least a portion of the side walls of channel 22 are formed to cooperate with the shape of slider 94 so as to guide slider 94 forward or rearward within channel 22 when horizontal screw 24 is turned, while not allowing slider 94 to displace vertically. Slider 94 slides forward or rearward within channel 22 in response to horizontal screw 24 being turned in the appropriate direction. The present invention contemplates side walls of channel 22 that are formed in any manner suitable to allow slider 94 to travel forward or rearward within channel 22, while not allowing slider 94 to displace vertically.

Connecting arm 96 is coupled to slider 94 and extends generally downward from slider 94, through the slot 97 of channel 22, to a region generally below upper arch 12. Lower arch 14 includes a lateral bar 98 that is operable to engage connecting arm 96 at its distal end. While engaged with connecting arm 96, lower arch 14 may move laterally in response to lateral motions, of the user's lower jaw. Connecting arm 96 may be integral to or separate from slider 94. Connecting arm 96 may be of variable length. Lateral bar 98 is shown with a substantially circular cross-section that allows coupling between connecting arm 96 and lateral bar 98, but other cross-sections of lateral bar 98 and manners of coupling connecting arm 96 and lateral bar 98 may be used without departing from the intended scope of the present invention.

Due to the relative positions of connecting arm 96 and lateral bar 98, when connecting arm 96 has engaged lateral bar 98, lower arch 14 and thus the user's lower jaw may be extended forward, relative to upper arch 12. The user's jaw may be adjusted in the same manner as described above in connection with FIGS. 2a–2d.

FIGS. 4a–4c illustrate exploded bottom, front, and side views of alternative embodiments of the present invention that include an alternative hooking element 26 constructed according to the teachings of the present invention. Hooking element 26 is vertically as well as forwardly adjustable, allowing it to be raised or lowered as necessary to customize device 10 for the particular user and breathing disorder being treated.

As shown in FIGS. 4b and 4c, vertical screw 30 extends downward from the exposed upper portion 23 of channel 22, through a threaded hole in the top of hooking element 26, until vertical screw 30 contacts flange 28, which is separate from hooking element 26. Vertical screw 30 may travel forward or rearward within exposed upper portion 23 of channel 22 when hooking element 26 and flange 28 slide within channel 22 in response to horizontal screw 24 being adjusted. Being exposed from the top, vertical screw 30 is operable to adjust the vertical displacement of hooking element 26 from flange 28. In one embodiment, vertical screw 30 is a set screw. Because flange 28 is prevented from moving vertically due to the shape of the side walls of channel 22, turning vertical screw 30 causes hooking element 26 to displace vertically, relative to upper arch 12. A removable cap 32 may be included in order to cover exposed upper portion 23 of channel 22 when vertical screw 30 is not being adjusted.

Due to the complimentary shapes of channel 22, hooking element 26, flange 28, and vertical screw 30, hooking element 26 is freely adjustable forwardly, rearwardly, and vertically. The ability of device 10 to be freely adjusted in this manner is a significant technical advantage over prior art devices, adding to the ease, effectiveness, and comfort of device 10 in improving breathing disorders. The present invention contemplates alternate embodiments wherein hooking element 26 is adjusted using a motor or hydraulics.

FIGS. 5a–5d illustrate exploded side views of alternative embodiments of the present invention. As shown in FIG. 5a, the vertical length of hooking element 26 is variable, such that the vertical distance between lower arch 14 and upper arch 12 may be increased. Hooking element 26 remains freely adjustable forwardly, rearwardly, and vertically. As shown in FIG. 5b, hook 44 may be fixedly attached or removably attached to hooking element 26. Hook 44 may be glued or otherwise affixed to hooking element 26, insertionally glued or force fitted into a hole drilled into hooking element 26, screwed into hooking element 26, or attached in any other manner to hooking element 26. As shown in FIG. 5c, the vertical length of hook 44 is also variable, such that an appropriate combination of hook 44 and hooking element 26 may be made in order to achieve the desired vertical displacement of lower arch 14, relative to upper arch 12. The fact that every such combination is not shown herein does not in any way limit the intended scope of the present invention.

FIG. 5d illustrates an alternative embodiment of hook 44 that includes a flexible member 46, such as a spring or rubberband, disposed between connector 16 and hook 44. When hook 44 has engaged hooking clasp 34 of lower arch 14 so as to extend the user's lower jaw forward, the jaw may still enjoy some freedom of movement due to flexible member 46. Not only does this configuration enable the user to be more comfortable when using device 10, flexible member 46 reduces any risk that the user's teeth may be injured as a result of quick and forceful movement of the user's lower jaw. Flexible member 46 may be incorporated into any of the embodiments described above or into any combination thereof, whether or not shown or described. In another embodiment, flexible member 46 is fixedly or removably attached to connector 16 at one end and fixedly or removably attached to lower arch 14 at the other end, coupling connector 16 to lower arch 12 directly. Other mechanisms designed to dampen the force transferred to and between upper arch 12 and lower arch 14 may be used without departing from the intended scope of the present invention.

Figure 6A:
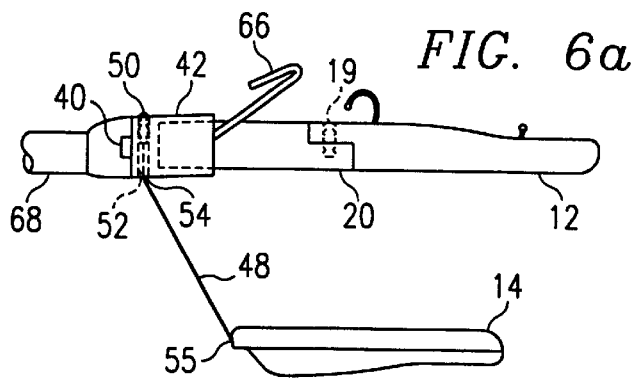
FIGS. 6a–6c illustrate exploded side views of alternative embodiments of the present invention adapted for use in connection with a tensile member.
Figure 6B:
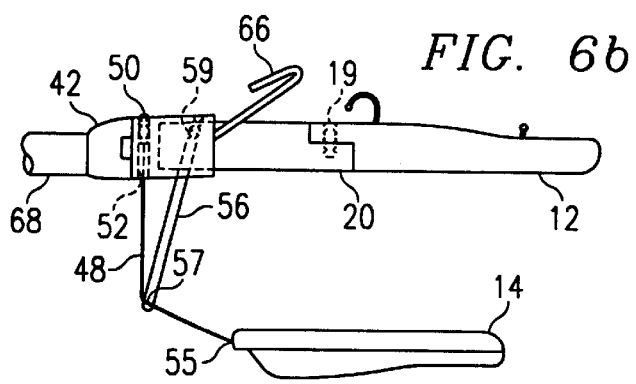
Figure 6C:
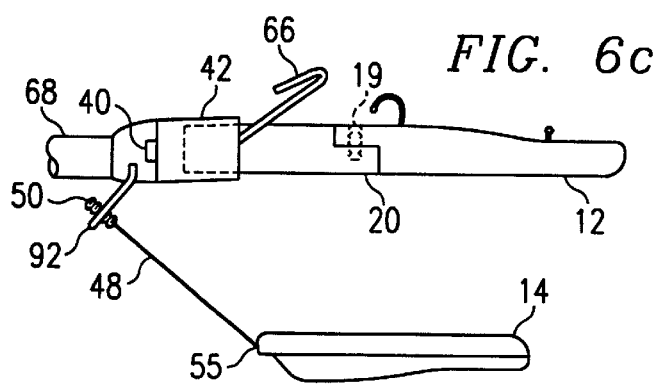

FIGS. 6a–6c illustrate side views of other embodiments of the present invention adapted for use in connection with a tensile member 48 under tension. According to one embodiment, tensile member 48 may comprise a monofilament line. According to alternate embodiments, tensile member 48 may be constructed in any shape and from any material suitable to extend the user's lower jaw forward when tensile member 48 is placed under tension, without departing from the intended scope of the present invention.

As shown in FIGS. 6a and 6b, tensile member 48 is secured to tension screw 50 at the generally top and forward surface of face plate 42 of connector 16. Tension screw 50 is operable to displace tensile member 48 in response to adjustment of tension screw 50. From its attachment at tension screw 50, tensile member 48 extends generally downward through hole 52, contacts support surface 54 as it leaves hole 52 at the generally bottom surface of face plate 42, and extends to attachment point 55 on lower arch 14. Attachment point 55 may be at any suitable location on lower arch 14. When tension screw 50 is adjusted, lower arch 14 is pulled in the direction of tensile member 48. The user's lower jaw is therefore extended forward, relative to upper arch 12. The present invention contemplates other suitable configurations of tension screw 50, hole 52, and support surface 54, so long as lower arch 14 is pulled generally forward in the direction of tensile member 48 when tension screw 50 is adjusted. In another embodiment, tensile member 48 is allowed to move freely through hole 52 unless a screw or other suitable member is adjusted to contact tensile member 48 within hole 52 and thereby press tensile member 48 against the inner surface of hole 52 with a force sufficient to secure tensile member 48 in the desired position. Tensile member 48 may be further adjusted by reducing or releasing the force pressing tensile member 48 against the inner surface of hole 52, moving tensile member 48 to the desired position, and then reapplying the force to tensile member 48. The present invention contemplates alternate embodiments wherein lower arch 14 is adjusted using a motor or hydraulics in connection with tensile member 48.

An important technical advantage of the present invention is that it allows the user's lower jaw to be adjustably positioned forwardly in response to tension directed from a point forward, relative to the user's lower jaw. The upward vertical component of the tension on lower arch 14 is decreased the more nearly horizontal the direction of tension placed on lower arch 14 using tensile member 48. As the upward vertical component of the tension decreases, so does the possibility that lower arch 14 will be pulled off the user's lower teeth when the mouth is opened or the lower jaw is moved. It is therefore desirable to direct the tension on lower arch 14 from a point forward of lower arch 14 and below attachment point 55 of tensile member 48 or as nearly horizontal with attachment point 55 as possible.

Hole 52 may be formed so as to cause tensile member 48 to contact the inner surface of hole 52 at support surface 54 before extending to attachment point 55. Tensile member 48 is thereby redirected such that the angle of its attachment to lower arch 14, relative to the horizontal, is more acute than it would be if tensile member 48 extended in a straight line between tension screw 50 and attachment point 55. The vertical component of the tension on lower arch 14 is thereby reduced. It should be understood that the positions and angles of hole 52 and support surface 54 may be varied in order to adjust the angle at which tensile member 48 attaches to lower arch 14, thereby adjusting the vertical component of the tension on lower arch 14.

As explained above, reducing the upward vertical component of the tension on lower arch 14 reduces the possibility that lower arch 14 will be pulled off the user's lower teeth when the mouth is opened or the lower jaw is moved. As shown in FIG. 6b, support arm surface 57 may be located near the distal end of support arm 56, which extends generally downward from connector 16 to a point generally forward of lower arch 14. Tensile member 48 contacts and is redirected by support arm surface 57. Tensile member 48 may also contact and be redirected by support surface 54. Support arm surface 57 is positioned vertically so as to allow tensile member 48 to exert a tensile force on lower arch 14 in a generally horizontal direction when tension screw 50 is appropriately adjusted. As discussed above, this provides an important technical advantage of the present invention.

Support arm 56 may be integral to or separate from connector 16. Support arm 56 may be fixedly coupled to connector 16, or may be coupled to connector 16 in a manner that allows support arm 56 to be extended or retracted by adjusting extension screw 59 in the appropriate direction. Variations in the manner of attachment of support arm 56 to device 10 and in the adjustability of support arm 56 are within the intended scope of the present invention. Using any such configuration to properly position support arm surface 57 vertically, through the positioning of support arm 56, the user or clinical-professional can reduce or eliminate the upward vertical component of the tension on lower arch 14.

In one embodiment, support arm surface 57 is provided by a hole in the distal end of support arm 56. In another embodiment, support arm 56 has a bifurcated distal end to constrain tensile member 48 laterally as it contacts and travels over support arm surface 57. Alternatively, a pulley 58 mounted on the distal end of support arm 56 provides support arm surface 57. Other configurations suitable to provide support arm surface 57 may be used without departing from the intended scope of the present invention.

FIG. 6c illustrates an embodiment of the present invention wherein the point at which tensile member 48 is coupled to connector 16 is generally below face plate 42. A mount 92 projects generally downward from connector 16 and adjustably couples tension screw 50, which is coupled to tensile member 48, to connector 16. As before, tensile member 48 is secured to lower arch 14 at attachment point 55, allowing lower arch 14 to be adjusted forwardly when tension screw 50 is turned. The location and vertical length of mount 92 may be varied as necessary to properly size device 10 to the user and to effectively treat the breathing disorder involved. The upward vertical component of the tension placed on lower arch 14 may be reduced or eliminated by configuring device 10 such that attachment point 55 is nearly level with or above the coupling of tensile member 48 to mount 92.

Figure 7:
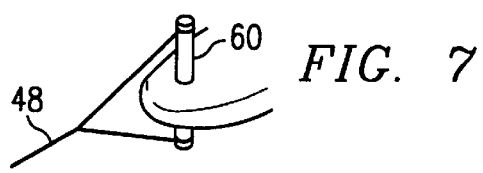
FIG. 7 illustrates an exploded side view of an alternative embodiment of the present invention adapted for use in connection with a tongue stud.

FIG. 7 illustrates an exploded side view of an alternative embodiment of the present invention adapted for use in connection with a tongue stud 60. Tongue stud 60 is made to pierce the user's tongue and is then secured to the remainder of device 10. Tongue stud 60 may be used in connection with any or all of the embodiments of the present invention described above to replace or combine with the functions of lower arch 14. For example, tongue stud 60 may be coupled to tensile member 48 in any of the embodiments illustrated in FIGS. 6a–6c. When used in connection with tensile member 48, tongue stud 60 is operable to extend the user's tongue forward when tension is placed on tensile member 48, thereby improving the breathing of the user. Although tongue stud 60 has been described most thoroughly in connection with tensile member 48, it should be understood that the present invention contemplates using tongue stud 60 in connection with any or all of the embodiments described above. For example, tongue stud 60 may be coupled to hook 44, hooking element 26, connecting arm 96, slider 94, or any other part of connector 16 in any or all of the embodiments discussed above. The present invention further contemplates alternate embodiments wherein tongue stud 60 is positioned using a motor or hydraulics.

Although the present invention and its advantages have been described in detail, it should be understood that various changes, substitutions, alterations, and modifications can be made herein without departing from the spirit and scope of the invention as defined by the appended claims.

What is claimed is:

1. A device for improving the breathing of a user, comprising:
   an upper arch adapted to receive at least some of the user's upper teeth;
   a lower arch adapted to receive at least some of the user's lower teeth; and a connector adjustably coupling the lower arch to the upper arch, the connector operable to adjustably position the lower arch forwardly, relative to the upper arch, by exerting a tensile force upon the lower arch;

the lower arch being adjusted from a first position corresponding to a first configuration of the upper arch, the lower arch, and the connector to a second position corresponding to a second configuration of the upper arch, the lower arch, and the connector.

2. The device of claim 1, wherein the connector is operable to allow lateral motion of the lower arch relative to the upper arch.

3. The device of claim 1, wherein the connector is operable to adjustably position the lower arch vertically relative to the upper arch.

4. The device of claim 1, wherein the connector is removably coupled to the upper arch.

5. The device of claim 1, further comprising a lip bumper.

6. The device of claim 1, wherein the upper and lower arches are adapted to receive a deformable material in which molds of at least some of the user's upper and lower teeth, respectively, may be formed.

7. The device of claim 1, wherein the upper and lower arches further comprise securing clasps to more fully secure the upper and lower arches to the user's teeth.

8. The device of claim 1, further comprising a face mask adjustably coupled to the connector.

9. The device of claim 1, further comprising:

a face mask adjustably coupled to the connector; and a gas supply system coupled to the face mask and operable to supply gas to the face mask at a positive air pressure.

10. The device of claim 1, further comprising:

a face mask;

a plurality of strap mounts coupled to the connector;

a head strap adjustably coupled to the face mask and adjustably coupled to the strap mounts; and a gas supply system coupled to the face mask and operable to supply gas to the face mask at a positive air pressure.

11. The device of claim 1, further comprising a tensile member coupled to the lower arch.

12. The device of claim 1, further comprising a set screw, the set screw adjusting the vertical position of the lower arch relative to the upper arch.

13. The device of claim 1, further comprising a flexible member removably coupled to the connector at one end and removably coupled to the lower arch at another end.

14. The device of claim 1, further comprising:

a flexible member having first and second ends;

a first mount coupled to the connector, the first end of the flexible member being removably coupled to the connector at the first mount; and a second mount coupled to the lower arch, the second end of the flexible member being removably coupled to the lower arch at the second mount.

15. A device for improving the breathing of a user, comprising:

an upper arch adapted to receive at least some of the user's upper teeth;

a lower arch adapted to receive at least some of the user's lower teeth;

a connector adjustably coupling the lower arch to the upper arch, the connector operable to adjustably position the lower arch forwardly, relative to the upper arch, by exerting a tensile force upon the lower arch;

a support surface associated with the connector, the support surface positioned forward of the lower arch; and a tensile member, the tensile member having first and second ends, the first end of the tensile member adjustably coupled to the connector, the second end of the tensile member coupled to the lower arch, the tensile member contacting the support surface along a contact region of the tensile member located between the first and second ends of the tensile member.

16. The device of claim 15, wherein the connector is operable to allow lateral motion of the lower arch relative to the upper arch.

17. The device of claim 15, wherein the connector is operable to adjustably position the lower arch vertically relative to the upper arch.

18. A device for improving the breathing of a user, comprising:

an upper arch adapted to receive at least some of the user's upper teeth;

a lower arch adapted to receive at least some of the user's lower teeth;

a connector adjustably coupling the lower arch to the upper arch, the connector operable to adjustably position the lower arch forwardly, relative to the upper arch, by exerting a tensile force upon the lower arch;

a support arm, the support arm having first and second ends, the support arm coupled to the connector at the first end;

a support arm surface located near the second end of the support arm; and a tensile member, the tensile member having first and second ends, the first end of the tensile member adjustably coupled to the connector, the second end of the tensile member coupled to the lower arch, the tensile member contacting the support arm surface along a contact region of the tensile member located between the first and second ends of the tensile member.

* * * * *